(12) United States Patent
Stewart et al.

(10) Patent No.: US 6,755,529 B2
(45) Date of Patent: Jun. 29, 2004

(54) METHOD AND APPARATUS FOR MEASURING CONTRAST SENSITIVITY

(75) Inventors: Jeffrey L. Stewart, Greenwich, CT (US); Stewart Weiss, Jackson Heights, NY (US)

(73) Assignee: Visionrx, Inc., White Plains, NY (US)

( * ) Notice: Subject to any disclaimer, the term of this patent is extended or adjusted under 35 U.S.C. 154(b) by 0 days.

(21) Appl. No.: 10/095,624

(22) Filed: Mar. 12, 2002

(65) Prior Publication Data

US 2003/0174284 A1 Sep. 18, 2003

(51) Int. Cl.[7] .................................................. A61B 3/02
(52) U.S. Cl. ..................................................... 351/243
(58) Field of Search ........................ 351/200, 205–207, 351/211, 221, 222, 246, 213–216, 239, 243; 600/558

(56) References Cited

U.S. PATENT DOCUMENTS

| | | | | |
|---|---|---|---|---|
| 4,365,873 A | * | 12/1982 | Ginsburg | 351/239 |
| 4,493,539 A | * | 1/1985 | Cannon, Jr. | 351/205 |
| 4,526,452 A | * | 7/1985 | Hirsch | 351/239 |
| 5,500,699 A | * | 3/1996 | Ginsburg | 351/239 |
| 5,539,482 A | * | 7/1996 | James et al. | 351/246 |
| 5,953,102 A | * | 9/1999 | Berry | 351/205 |
| 6,045,515 A | * | 4/2000 | Lawton | 351/239 |

* cited by examiner

*Primary Examiner*—Dennis Ruhl
*Assistant Examiner*—John R. Sanders
(74) *Attorney, Agent, or Firm*—J. De La Rosa

(57) ABSTRACT

A novel contrast sensitivity test utilizing an adaptive contrast threshold algorithm is proposed. The contrast sensitivity test is embodied as a two-alternative forced choice examination using grating stimuli of randomly interleaved spatial frequencies. The stimulus's orientation is either tilted to the left or right of vertical. During an examination, a succession of grating stimuli is presented to the subject, and the subject asked to indicate the orientation of each stimulus. The contrast level for the next stimulus is varied depending on the subject's response to the previous one using an adaptive weighted up-down algorithm. For each correct response, the contrast level is reduced, whereas for each incorrect response the contrast level is increased. Importantly, the amount by which the contrast level is lowered is different from the amount by which it is raised, and as the examination progresses, the amount changes. A maximum likelihood method is then employed for finding the best estimation of the contrast threshold from the subject's responses to known contrast levels.

33 Claims, 6 Drawing Sheets

METHOD AND APPARATUS FOR MEASURING CONTRAST SENSITIVITY

TECHNICAL FIELD

The present invention relates to a method and apparatus for measuring the contrast sensitivity of the human eye.

BACKGROUND OF THE INVENTION

In recent years, it has been recognized that contrast is an important parameter for assessing vision. Although visual acuity tests can be used to detect changes in the spatial resolving capability of the human eye, used alone it is typically inadequate for measuring the eye's performance when subjected to glare or reduced light environments and for measuring vision loss not caused by refractive error. Often, the human eye will lose its ability to perceive patterns, i.e., contrast, even though visual acuity is still normal. Indeed, the first indication of certain eye pathologies is a loss of contrast sensitivity.

Contrast sensitivity determines the lowest contrast level which can be detected by a subject for a given size target, defined in terms of spatial frequency. Normally, a wall-mounted chart printed with circular patches of sine wave gratings, which decrease in contrast from left to right, and increase in spatial frequency from top to bottom, is used to measure contrast sensitivity. The gratings are either vertical, or tilted at 10 degrees to the left or right of vertical. During an examination, the subject is asked to identify the orientation of the grating patches, moving from left to right for each row. For each row or spatial frequency, the contrast level of the last grating patch's orientation correctly identified is the contrast threshold. The reciprocal of this contrast threshold is commonly known as the contrast sensitivity.

Efforts to automate contrast sensitivity measurements include the use of computer controlled monitor-based systems. In these latter systems, vertical sinusoidal gratings are displayed on a high-resolution monitor controlled by a computer, again for varying contrast levels. This is done by incrementally increasing the spatial frequency in predetermined steps. More specifically, while incrementing spatial frequency, the contrast level is varied according to a contrast control algorithm for determining the minimum amount of contrast needed for the subject to see the grating. As noted, this minimum contrast level is called the contrast threshold. Typically, the contrast control algorithm either increases or decreases the contrast level according to whether the previous grating was seen or not seen, and continues until the contrast level oscillates about the contrast threshold. Typically, when the subject correctly responds three times, then the contrast level is decreased by one step. An incorrect response leads, however, to a one step increase in the level.

Another approach involves progressively increasing the contrast level until the subject reports seeing the grating, and then progressively decreasing the contrast until the subject reports not seeing the grating. The contrast threshold is taken as the average of the contrast levels of when the subject reports seeing and not seeing the grating.

Although such contrast sensitivity measurement systems as well as other psychophysical methods work reasonably well, it is somewhat time-consuming for them to measure the contrast threshold with a high degree of accuracy. Accordingly, it would be desirable to have a method and system for measuring the contrast sensitivity which is more efficient and accurate.

SUMMARY OF THE INVENTION

A novel contrast sensitivity test utilizing an adaptive contrast threshold algorithm is proposed. The contrast sensitivity test is embodied as a two-alternative forced choice examination using grating stimuli of randomly interleaved spatial frequencies. The stimulus's orientation is either tilted to the left or right of vertical. During an examination, a succession of grating stimuli is presented to the subject, and the subject asked to indicate the orientation of each stimulus. The contrast level for the next stimulus is varied depending on the subject's response to the previous one using an adaptive weighted up-down algorithm. For each correct response, the contrast level is reduced, whereas for each incorrect response the contrast level is increased. Importantly, the amount by which the contrast level is lowered is different from the amount by which it is raised, and as the examination progresses, the amount changes. A maximum likelihood method is then employed for finding the best estimation of the contrast threshold from the subject's responses to known contrast levels.

In one embodiment, the grating stimulus consists of dark and light bars having a luminance which varies in a sinusoidal manner. Alternatively, the luminance can vary in a square-wave manner. In another embodiment, the grating stimulus consists of color bars either tilted to the left or right of vertical. Either the luminance or saturation can be varied sinusoidally from a maximum to a minimum. Likewise, a square wave color grating may also be used. Characteristic changes in the subject's contrast sensitivity for the different spatial frequencies may be used to detect certain eye diseases and disorders.

BRIEF DESCRIPTION OF THE DRAWINGS

The features and advantages of the present invention will become more readily apparent from the following detailed description of the invention in which like elements are labeled similarly and in which.

DETAILED DESCRIPTION

In accordance with the principles of the invention, a novel contrast sensitivity test utilizing an adaptive contrast threshold algorithm is proposed. The contrast sensitivity test is embodied as a two-alternative forced choice examination using grating stimuli of randomly interleaved spatial frequencies. The stimulus's orientation is either tilted to the left or right of vertical. The grating stimuli are displayed on a high-resolution monitor, with the contrast level varied according to whether the subject correctly identified the orientation of the previous grating stimulus. In general, the contrast control algorithm is an adaptive weighted up-down algorithm. For each correct response, the contrast level is reduced, whereas for each incorrect response the contrast level is increased. Importantly, the amount by which the contrast level is lowered is different from the amount by which it is raised, and as the examination progresses, the amount changes. In this manner, the set contrast level quickly converges with a high certainty to the "contrast threshold," that is, the minimum amount of contrast needed for the subject to detect the stimulus.

Those skilled in the art will note that the reciprocal of the contrast threshold is called the contrast sensitivity (CS). A higher contrast sensitivity simply implies that a lower contrast level is required for detecting the orientation of the grating. A plot of the contrast sensitivity versus spatial frequency is commonly known as the contrast sensitivity function (CSF). It is this spatial contrast function that the present visual measurement system is measuring.

Figure 1:
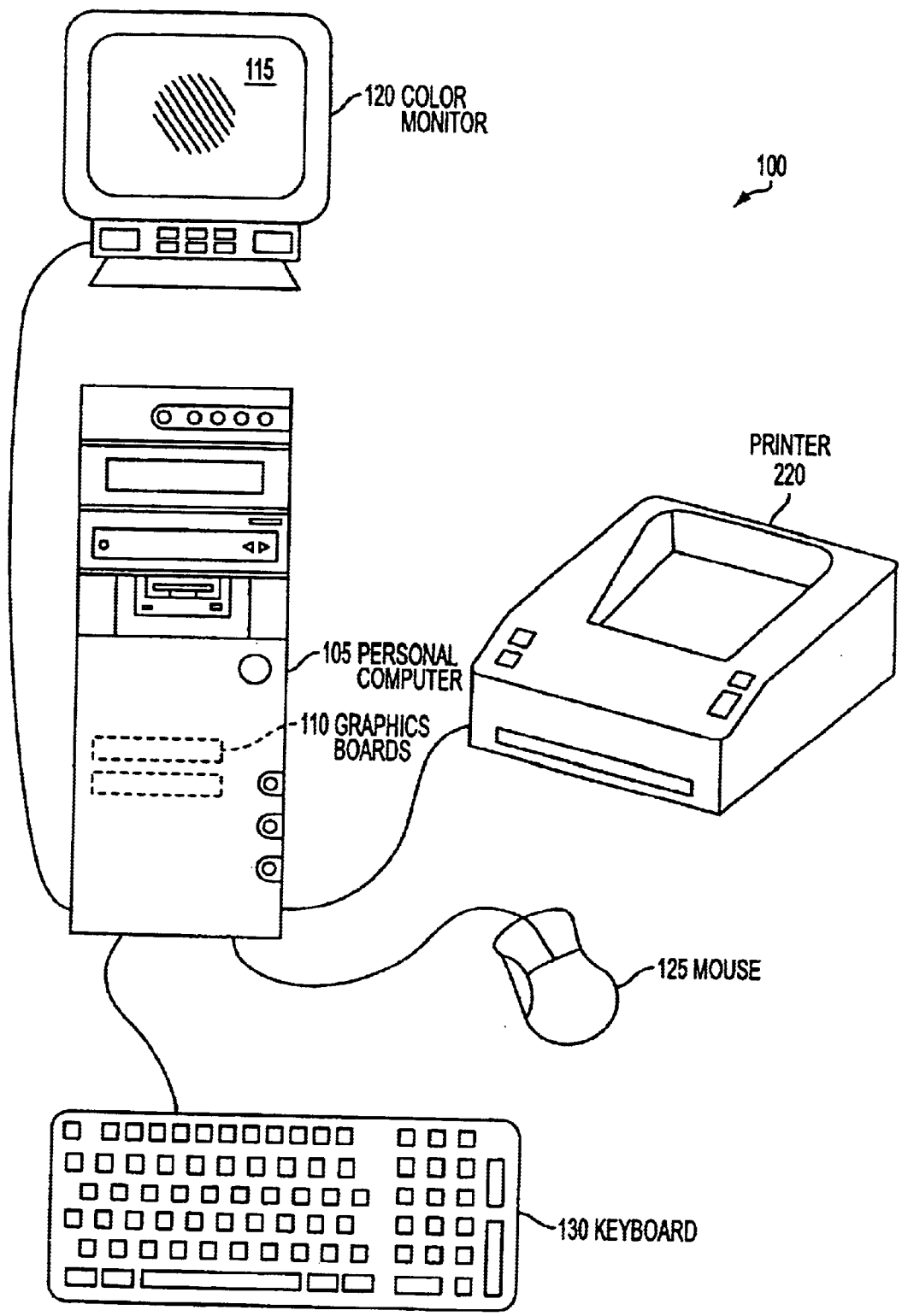
FIG. 1 depicts a contrast sensitivity measurement system in accordance with the principles of the present invention.

Shown in FIG. 1 is a simplified block diagram of a contrast sensitivity measurement system 100 in accordance with the principles of the invention. Contrast sensitivity measurement system 100 comprises a computer 105, such as a personal computer (PC) running under Windows. Computer 105 includes conventional graphics boards 110 which may be readily programmed to display grating stimuli 115 of randomly interleaved spatial frequencies, and varying contrast levels on a monitor 120. In addition to displaying grating stimuli 115, computer 105 monitors the subject's response thereto, which is entered by, preferably, clicking buttons on a computer mouse 125, using keyboard 130, or speaking into a microphone, among other methods.

Figure 2:
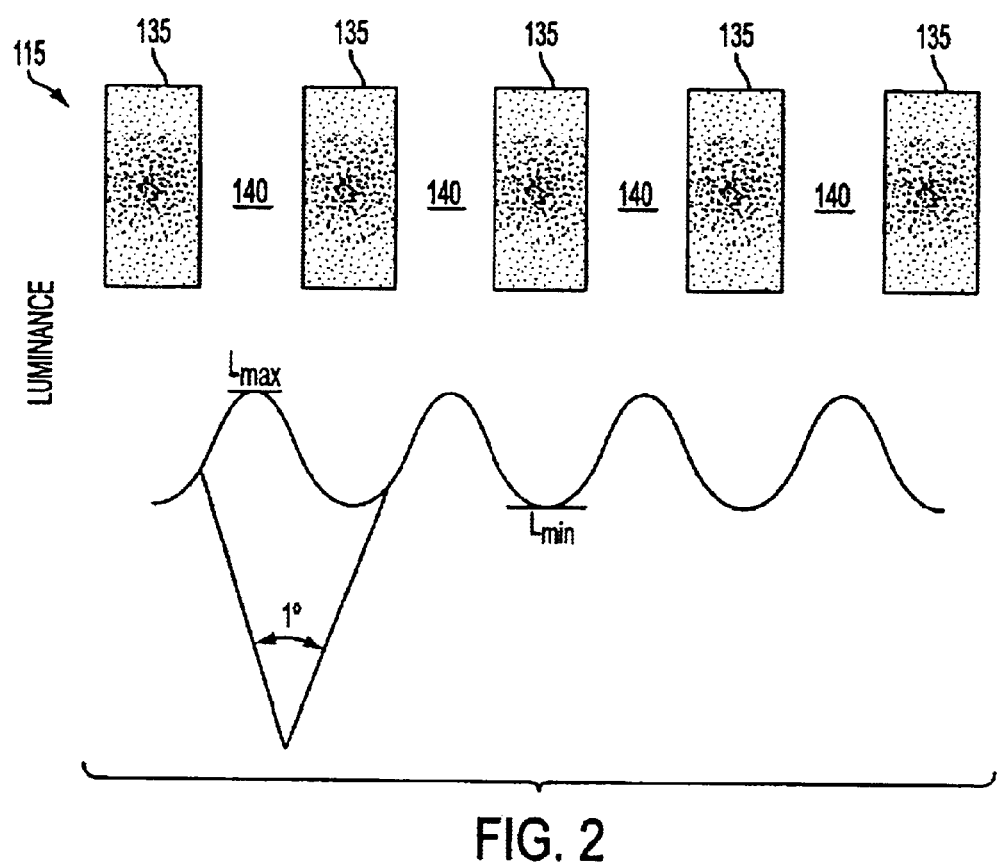
FIG. 2 depicts an illustrative grating stimulus, along with its luminance profile.

Referring to FIG. 2, grating stimulus 115 consists of dark and light bars 135, 140, respectively, having a luminance which varies in a sinusoidal manner between a maximum $L_{max}$ and minimum $L_{min}$, or a so-called sinusoidal grating. The contrast level of the grating stimuli is the functional relationship of the maximum and minimum luminance levels, expressed as follows:

$$C = \frac{L_{max} - L_{min}}{L_{max} + L_{min}} \quad \text{Eq. (1)}$$

where C is the contrast level, $L_{max}$ is the maximum luminance level, and $L_{min}$ is the minimum luminance level. It is of interest to note that the contrast level, C, of the grating stimulus can be varied without changing the average luminance of the screen displaying the grating stimulus. Although the contrast level varies between 0 and 1, hereinafter the contrast level will be expressed as a percentage varying instead between 0 and 100.

Alternatively, square wave grating stimuli may be used, similarly having light and dark bars, but having a luminance which varies in square-wave manner between a maximum and minimum. Likewise, the contrast level may be expressed in the above manner.

In either case, the size of the bars of the grating stimulus is expressed in terms of the number of cycles per degree subtended at the eye, with one cycle consisting of one light bar and one dark bar. In the art, this is called the spatial frequency of the grating, having a unit of cycles per degree (cpd).

In the preferred embodiment, the subject views high-resolution color monitor 120 at a predetermined distance for each of the grating stimuli to subtend an angle corresponding to the desired spatial frequencies. Of course, the subject may view the grating stimuli monocularly, with each eye tested separately. An operator may be seated at or near computer 105 for controlling the test, or the testing may be fully automated, or even conducted through the Internet.

A single grating stimulus is displayed at any given time, tilted to the left or right of vertical, for example 30 degrees. The subject is then asked to identify which orientation the grating had by clicking on either a left-leaning or right-leaning image displayed on the screen, and as such, is forced to choose one of the two possible orientations. The answer is either correct or incorrect, making the examination a two-alternative forced choice examination. The presentation of the grating stimulus and the subject's response thereto hereinafter is called a "trial." A sequence of trials at a single spatial frequency is hereinafter called a "chain." As such, each chain or, more accurately, each examination chain is a sequence of grating stimuli of a fixed spatial frequency, but of a varying contrast level and orientation, along with the subject's responses.

The contrast sensitivity examination consists of "chains" at randomly interleaved spatial frequencies, preferably, the five spatial frequencies of 2, 4, 6, 12 and 18 cycles per degree. That is, the spatial frequencies are presented in random order. At the start of each chain, the contrast level is set to an initial value for its spatial frequency, Initial_stimulus[f], where f is the number corresponding to one of the test spatial frequencies. A grating stimulus having this initial contrast level is then displayed to the subject. The contrast level of the next stimulus, however, depends on whether the subject correctly identified the orientation of the previous grating stimulus. The rule is to increase the contrast level by an amount labeled, S_up, if the subject responds incorrectly, and to decrease it by an amount, labeled S_down, if the subject responds correctly. Although the amounts by which it is increased or decreased are different, and change as the examination progresses, the ratio of the amounts, S_up/S_down remains constant throughout the entire examination. Note that the contrast level is varied by adjusting the range of the luminance, $L_{max}$ to $L_{min}$, and preferably by equally varying these latter values.

In this latter manner, the set contrast level quickly converges. The objective of the algorithm, which is the same for all chains, is to find the contrast threshold for each spatial frequency. This contrast threshold is the contrast level for which the subject with a certain probability correctly identifies the orientation of the stimulus.

Recall that the present method, however, is a two-alternative forced choice procedure which forces the subject to choose from two alternative choices, one of which is the correct response. Since human subjects are not perfect observers, the contrast threshold is defined in probabilistic terms. The observable result of varying the contrast level is the subject's response. In other words, the percentage of correct responds is a function of the contrast level. That is, high contrast levels will always be seen, while certain low levels will never be seen. The fraction of seen stimuli as a function of the contrast level is commonly referred to as the psychometric function and typically appears as an S shaped curve (an "ogive") It is this psychometric function which is constructed for determining the contrast threshold in probabilistic terms.

On the basis of this psychometric function, we assume that if p is the target threshold probability, then the sequence of contrast levels should converge to a value X_p such that the probability of correctly identifying the orientation of the stimulus with a contrast level X_p is p. Preferably, the target threshold probability is set to 0.75 for each chain. This is reasonable since in forcing the subject to choose from two alternative choices there is already a 50% chance of a correct response.

Now, the equilibrium condition for convergence to a contrast level X_p is $$S\_up*(1-p)=S\_down*p \quad \text{Eq. (2)}$$

or equivalently $$S\_up/S\_down=p/(1-p) \quad \text{Eq. (3)}$$

Accordingly, if it is desired that the examination converges to 75% correct responses (p=0.75), then the ratio of the upward and downward steps, S_up/S_down, is 3. In other words, an incorrect response causes the contrast level to increase three times as much as a correct response causes it to decrease. Importantly, as the examination progresses, the amount by which the contrast level either increases or decreases changes, but the ratio remains the same.

Preferably, the downward step, S_down, is set equal to a variable labeled step_size whose initial value may be varied to change the duration of the test, and the reliability of the measured threshold. As the initial step size increases, the test duration increases, and the threshold reliability increases. The variable step_size is used to calculate the amount by which the contrast level will be changed in the next trial. As noted, with the downward step S_down set to step_size (i.e., S_down=step_size), then the upward step, S_up is always step_size*p/(1-p). At the start of each chain, the step_size is initially set to 16, but then varies as the examination progresses. And, as such, the amount by which the contrast is increased or decreased varies as the examination progresses. Recall that each correct response leads to a decrease, and each incorrect response leads to an increase in contrast level. The amounts by which the contrast levels are lowered or raised are different, and calculated on the basis of the current value of step_size.

Mathematically, each chain can be expressed as sequence of contrast levels, $a_0, a_1, a_2 \ldots, a_n$. Recall that the contrast level is set based on the subject's response to the previous grating stimulus, and the current value of the step_size. Again the rule is that an incorrect response causes the contrast level to increase, while a correct response causes it to decrease.

A contrast level $a_j$ is considered a reversal point within the chain if one of the following conditions is true, defining local maxima and minima in the sequence of the contrast levels that results from increasing and decreasing the contrast levels depending on the subject's response to the previous stimulus:

$$a_{j-1}<a_j \text{ and } a_{j+1}<=a_j \text{ local maximum} \quad \text{Eq. (4)}$$

$$a_{j-1}<=a_j \text{ and } a_{j+1}<a_j \text{ local maximum} \quad \text{Eq. (5)}$$

$$a_{j-1}>a_j \text{ and } a_{j-1}>=a_j \text{ local minimum} \quad \text{Eq. (6)}$$

$$a_{j-1}>=a_j \text{ and } a_{j+1}>a_j \text{ local minimum} \quad \text{Eq. (7)}$$

Normally, a reversal occurs if the contrast level was increasing, and the subject then correctly identifies the orientation of the grating stimulus, or if the contrast level was decreasing and the response then incorrectly identifies the orientation. In a chain, if there is no intervening reversal point between the reversal points $a_j$ and $a_k$, them the sequence of points $a_j, a_{j+1} \ldots a_{k-1}, a_k$ is defined as a run. Runs have either an up or down orientation, with the orientation of adjacent runs always opposite.

Figure 3:
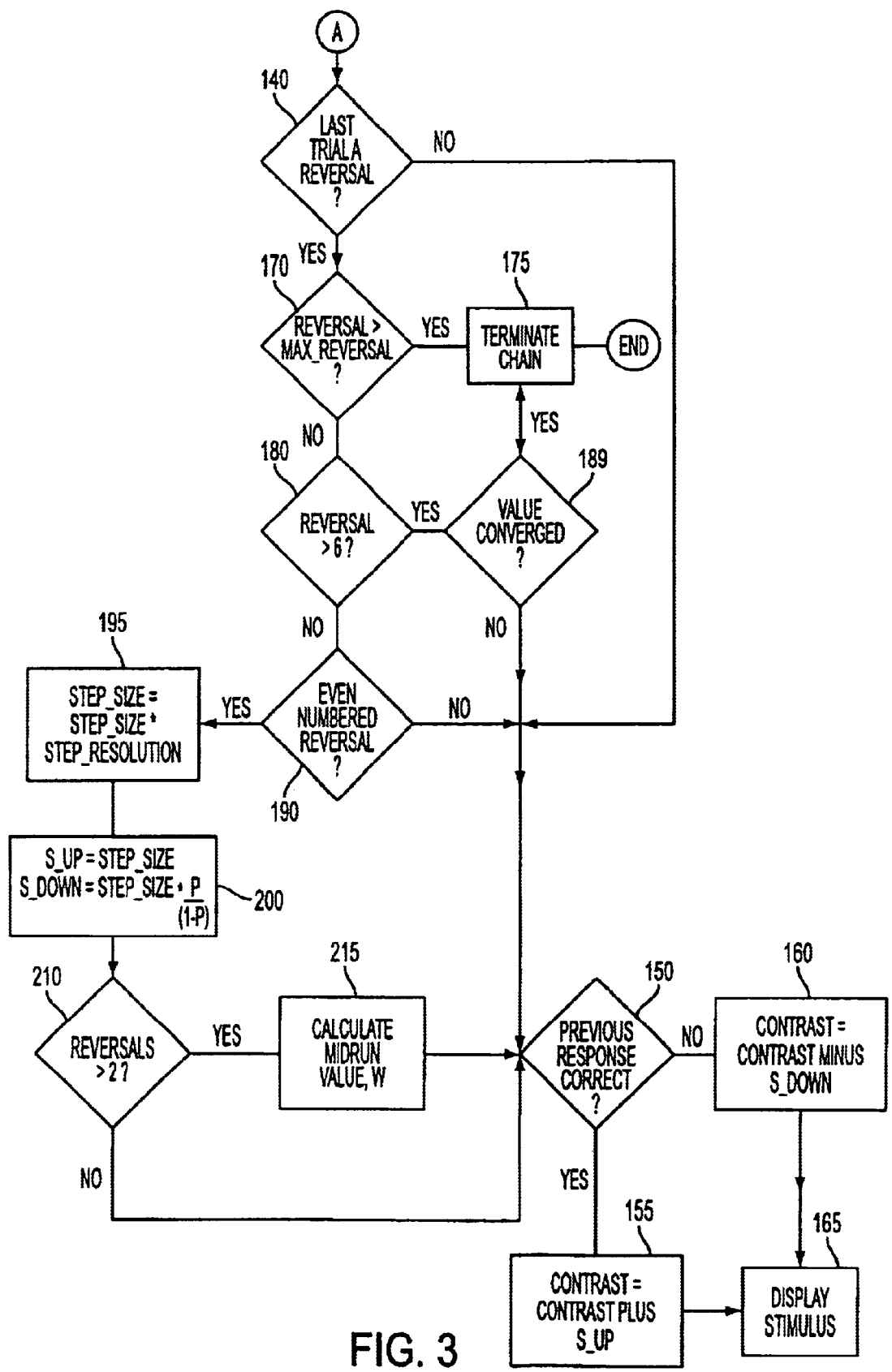
FIG. 3 depicts a flowchart for the contrast control algorithm of the present invention.

FIG. 3 depicts a flowchart for adjusting the contrast level for each chain, namely the step size by which the contrast level is varied. It should be understood that the examination parameters are initialized at the start of each chain. The examination parameters may be initialized to customize the test for speed versus accuracy. The default values are as follows:

| NAME | VALUE | DESCRIPTION |
| --- | --- | --- |
| Max_stimulus | 100 | Largest contrast level |
| Min_stimulus | 0 | Smallest contrast level |
| Max_reversals | 6 | Stopping criterion for a chain |
| Step_reduction | 0.5 | Fraction to diminish step_size |
| Step_size | 16 | Size of starting step |

Now referring to the flowchart of FIG. 3, each time a chain is run, a check is made at step 140 to determine if the last trial was a reversal point. If the previous trial was not a reversal, then the step_size remains the same, and the general rule is then applied: an incorrect response increases the contrast level and a correct response decreases it (steps 150, 155, 160).

However, if the previous trial was a reversal, then the following actions are performed:

if the number of reversal points is greater than the value, Max_reversal, then the chain terminates (steps 170, 175).

if there are more than six reversals (step 180), a convergence test is applied (step 185). Preferably, the convergence test is whether the last three peaks or valleys are rising or falling together. If so, the chain terminates (step 175). Otherwise, the general rule is applied to the contrast level for the next trial (steps 150, 155, 160).

after every even-numbered reversal, the step_size is reduced by a constant factor as follows (steps 190, 195):

$$\text{step\_size=step\_size*step\_reduction}$$

where 0<step_reduction<1, preferably 0.5.

and then S_up and S_down recomputed on the basis on the new step_size (step 200), with S_up=step_size and S_down=step_size*p/(1-p);

if the reversal, however, is an even-numbered reversal greater than 2 (step 210), the mean contrast level, ω, of the reversal points are calculated, e.g., the midrun value (step 215). This midrun value is later used in scoring, that is, estimating the contrast threshold for each chain. Again, the general rule is applied: an incorrect response increases the contrast level, and a correct response decreases it (steps 150, 155, 160);

Listed below is an illustrative pseudo-code for the above algorithm for adjusting the contrast level within each chain after a stimulus has been displayed and the response thereto has been recorded.

```
Check whether a reversal occurred in the last trial;
If a reversal occurred, then
    If the number of reversals > Max_reversals then
        terminate chain;
    Otherwise, if the number of reversals is even then
        If the number of reversals >= 6 then
            Check convergence;
            If chain has converged, then
                terminate chain;
```

-continued

```
        End If
      End If
      If the number of reversals > 2 then
         Compute the mid-run value
      End if
      Set the new step_size=step_size* step_reduction
      Set S_up=step_size;
      Set S_down=S_up*target_thresh/(1-target_thresh);
    End if
  End if
  If the last trial was a correct response then
      Set contrast_level=contrast_level - S_down;
  Otherwise
      Set contrast_level=contrast_level_S_up;
```

Once all the chains have been terminated, each spatial frequency has to be so-called "scored," that is analyzed using a maximum likelihood method for determining the contrast threshold, or the contrast level for which there is the desired percentage of correct responses from the subject, here 0.75.

For a forced choice procedure having m alternative choices, the psychometric function takes the following general form, and is used to determine the contrast threshold for each chain. Recall that this psychometric function is the percentage of seen stimuli versus contrast level.

$$\psi(x; \alpha, \beta, \gamma, \lambda) = \lambda + (1 - \gamma - \lambda)\left(1 - 2^{(-\frac{x}{\alpha})^\beta}\right) \quad \text{Eq. (8)}$$

where the function $\psi$ is the percentage of seen grating stimuli, x is the contrast level, $\gamma$ is the inverse of the number of alternative choices, or 1/m. The $\lambda$ parameter is the lapse rate of the subject, or the fraction of levels missed because of noise, e.g., distractions, human error, etc. For purposes herein, the $\lambda$ parameter is limited between 0 and 0.05. The $\beta$ and $\lambda$ parameters are unknown parameters used for fitting the psychometric function to the subject's responses for the known contrast levels.

For each spatial frequency, the last computed midrun value $\omega$ is used as the preliminary estimated contrast threshold. This midrun value $\omega$ is the weighted average of all but the first two reversal points. The algorithm can give more weight to the reversal points of later runs in order to make the measured threshold less dependent on early errors in test-taking. For each contrast level $x_i$ in the chain, let $n_i$ be the number of trials at that level, and let $s_i$ be the number of trials with the correct response. Also, let H be the total number of distinct contrast levels for which there are trials in the chain, and let $$n = \sum_{i=1}^{H} n_i \quad \text{Eq. (9)}$$

Then, n is the total number of trials in the chain.

In obtaining an estimation of the contrast threshold, we try to find the values of the parameters $\alpha$, $\beta$, and $\lambda$ that would most likely produce the responses we in fact observed. This, however, is exactly what the likelihood function $L(x|\psi)$ defines, which is obtained by reversing the roles of x and $\psi$.

Given the above, the maximum likelihood function $L(x|\psi)$ for the data set of contrast levels can then be expressed as:

$$L(x \mid \alpha, \beta, \gamma, \lambda)) = \prod_{i=1}^{H}\left[\frac{n_i!}{s_i!(n_i - s_i)!}\psi(x_i; \alpha, \beta, 0.5, \lambda)^{S_i}(1 - \psi(x_i; \alpha, \beta, 0.5, \lambda))^{n_i - s_i}\right] \quad \text{Eq. (10)}$$

The task of finding the contrast threshold then requires finding the values of $\alpha$, $\beta$, $\lambda$ that maximize L(x). This can be readily accomplished, for example, using the Powell's direction set function minimization algorithm wherein the values $\alpha$, $\beta$, and $\lambda$ can be solved by minimizing $-L(x)$. For a description of this latter minimization algorithm, see Numerical Recipes, W. H. Press et al, which is incorporated herein by reference.

Using this minimization algorithm, the computed values of $\alpha$, $\beta$, and $\lambda$ are then inserted back into the psychometric function, Eq. (8), to find x' for which $\psi(x', \alpha, \beta, \gamma, \lambda)$ equals 0.75. This value x' is the maximum likelihood estimate of the contrast threshold. It can be shown that if $\log(x'/\omega)$ is sufficiently small, then $\omega$ is an acceptable value for the contrast threshold.

Of course, the above procedure is repeated for each chain to establish the contrast threshold for different spatial frequencies from which the spatial frequency contrast function can be readily computed. Importantly, the spatial frequencies are randomly displayed to reduce the probability of guessing by the subject. Furthermore, it is contemplated that grating stimuli whose orientations are easily detected are presented to the subject to keep the subject from getting discouraged or fatigued. These so-called "bogus stimuli" are not used in scoring, and run less frequently than other chains. If desired, simple contrast control algorithms may be used, such as an ascending or descending staircase algorithm. Preferably, a bogus stimulus is displayed every fifth display. A bogus_periodicity parameter can be set at initialization to set the frequency at which they appear in the examination.

Software to implement the above described contrast sensitivity measurement therefore includes displaying a chain of grating stimuli at randomly interleaved spatial frequencies, recording the subject's response to the orientation of the stimuli, and adjusting the contrast level in accordance with the above described procedure. Once the examination is completed, a maximum likelihood method is employed for finding the best estimation of the contrast threshold from the subject's responses to the known contrast levels. This is done on a probabilistic basis. Such software is easily written by those skilled in the art who have been equipped with the understanding of the operation of the present invention as set forth herein, and may be written in C++, or other programming languages.

If desired, a plot of the contrast sensitivity versus spatial frequency can be generated, and graphically displayed on the monitor or on a printer 220. This so-called "contrast sensitivity function" (CSF) can be saved on hard disk, recalled for later use, imported into a database, and/or transmitted to a remote location.

Figure 4:
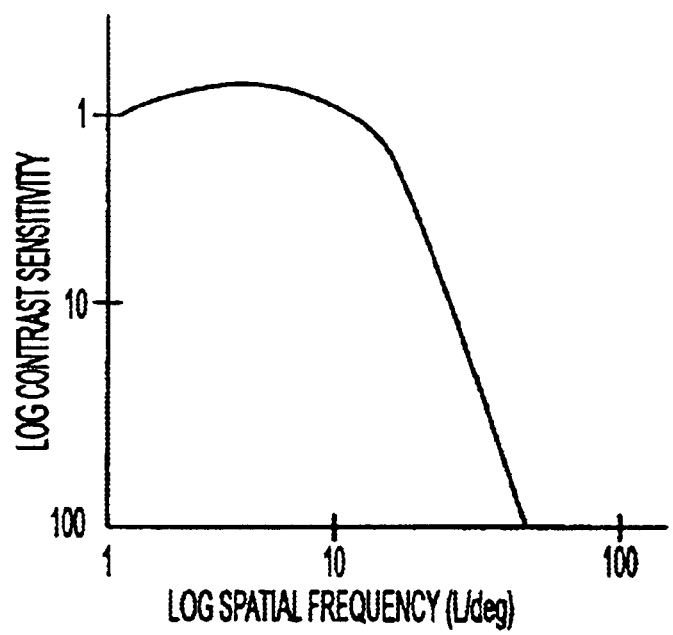
FIG. 4 depicts an illustrative plot of contrast sensitivity versus spatial frequency.

Shown in FIG. 4 is a typical contrast sensitivity measurement. It resembles a band-pass function with the peak at a mid-spatial frequency, and only under high contrast is the resolution at its maximum. Although the actual shape and critical cutoff frequencies are highly dependent on a number of factors, such as the mean luminance set at initialization, it provides a good measurement of the functioning of the human visual system, providing early detection of certain eye diseases or disorders. For example, subjects with multiple sclerosis typically have contrast sensitivity losses at low spatial frequencies, while those with cataracts have an overall reduction in contrast sensitivity. Amblyopia generally results in contrast sensitivity losses at high spatial frequencies, as well as an overall reduction. Therefore, such a mapping of the contrast sensitivity affords a qualitative way to detect and distinguish different visual disorders.

Figure 5:
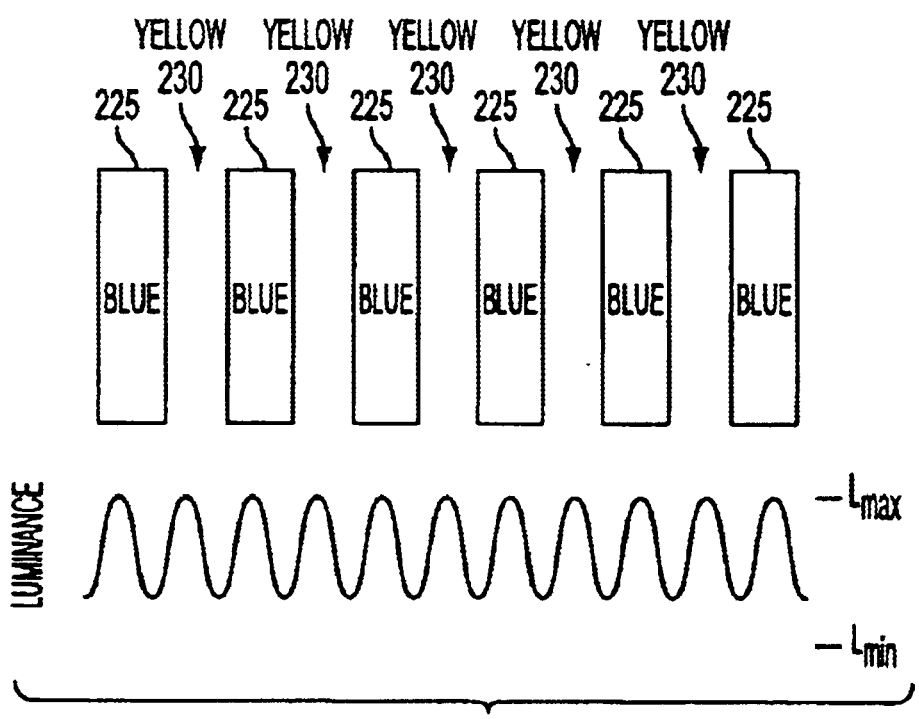
FIG. 5 depicts a color grating stimulus along with its luminance profile in accordance with the principles of the present invention.

In another embodiment of the invention, grating stimulus 115 instead consists of color bars 225, 230, as shown in FIG. 5, which are presented either tilted to the left or right of vertical (not shown for the sake of simplicity). Again, the spatial frequencies are randomly interleaved. The luminance, however, varies sinusoidally from a maximum, $L_{max}$, at the center to a minimum, $L_{min}$ at the edge of each color bar. Preferably, the colors are complementary colors, such as the complementary color pair of blue and yellow. In this latter embodiment, the contrast can likewise be expressed by Eq. 1. During an examination, a succession of color grating stimuli of randomly interleaved spatial frequencies can be presented to the subject. Similarly, the subject is asked to indicate the orientation of the color gratings, and the contrast level for the next stimulus then varies depending on the subject's response to the previous one, as discussed above herein. Again, the contrast level is preferably adjusted by equally varying the range of the luminance, that is $L_{max}$ and $L_{min}$. Measuring the contrast sensitivity as a function of spatial frequency for different color pairs may be useful in the early detection of certain eye diseases or disorders.

Figure 6:
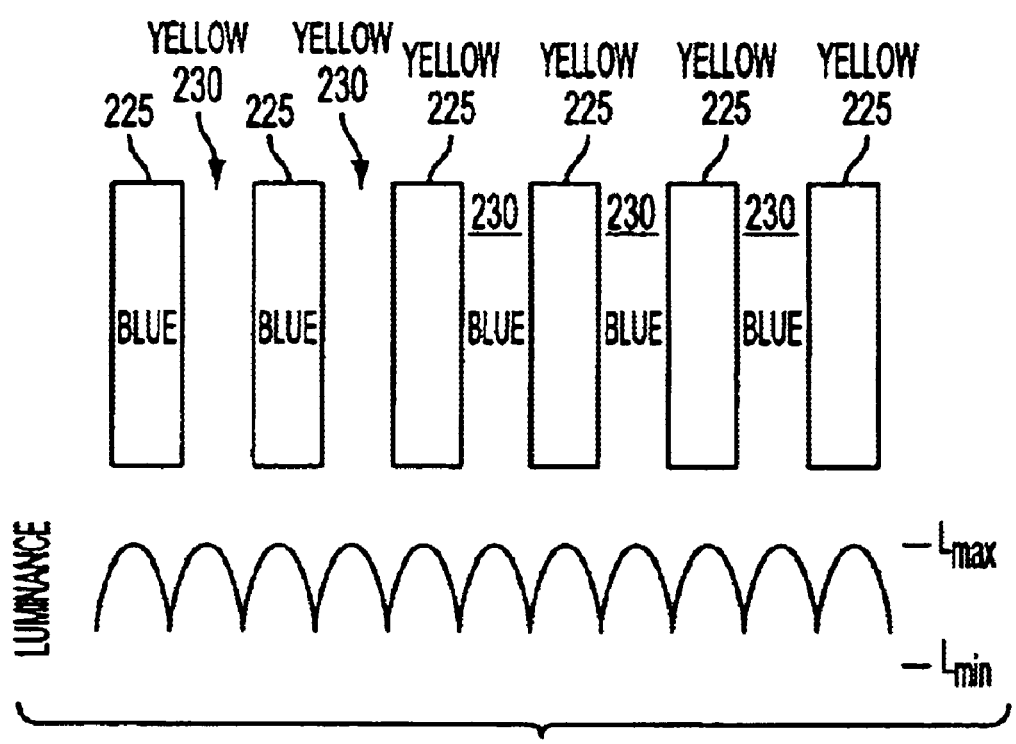
FIG. 6 depicts another color grating stimulus having an alternative luminance in accordance with the principles of the present invention.

Alternatively, the luminance can vary from a maximum, $L_{max}$, at the center to a minimum, $L_{min}$ at the edge of each color bar, but in a so-called half wave sinusoidal manner, as depicted in FIG. 6.

Figure 7:
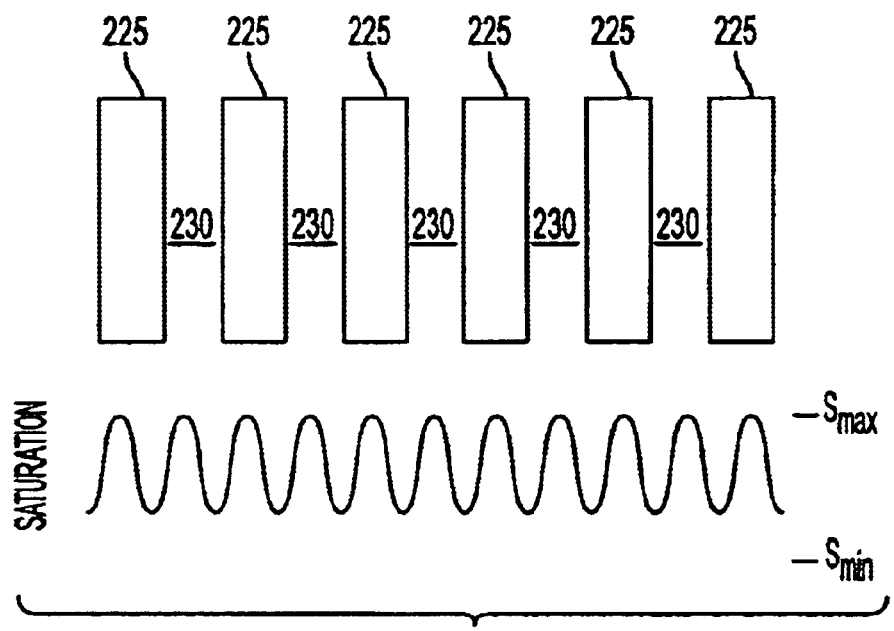
FIG. 7 depict another color grating stimulus along with its saturation profile in accordance with the principles of the present invention.

In another embodiment of the present invention, the color saturation S may be varied sinusoidally from a maximum to a minimum, while the luminance is held constant for the color gratings, as depicted in FIG. 7. Saturation refers to the amount of dilution of the pure color or hue with neutral gray of the same luminance, as commonly used in the field of colorimetry. The saturation S varies from 0 to 1, and has a maximum purity at S=1. It should be understood that as S is decreased, each color moves toward gray. A pseudo-color contrast can likewise be defined in terms of the maximum and minimum saturation levels as follows, and an examination conducted accordingly.

$$C = \frac{S_{max} - S_{min}}{S_{max} + S_{min}} \quad \text{Eq. (11)}$$

where C is the pseudo-color contrast level, $S_{max}$ is the maximum saturation level, and $S_{min}$ is the minimum saturation level. Preferably, the pseudo-color contrast is varied only by adjusting the maximum saturation $S_{max}$ so that both colors are closer to gray or both are farther from gray.

Figure 8:
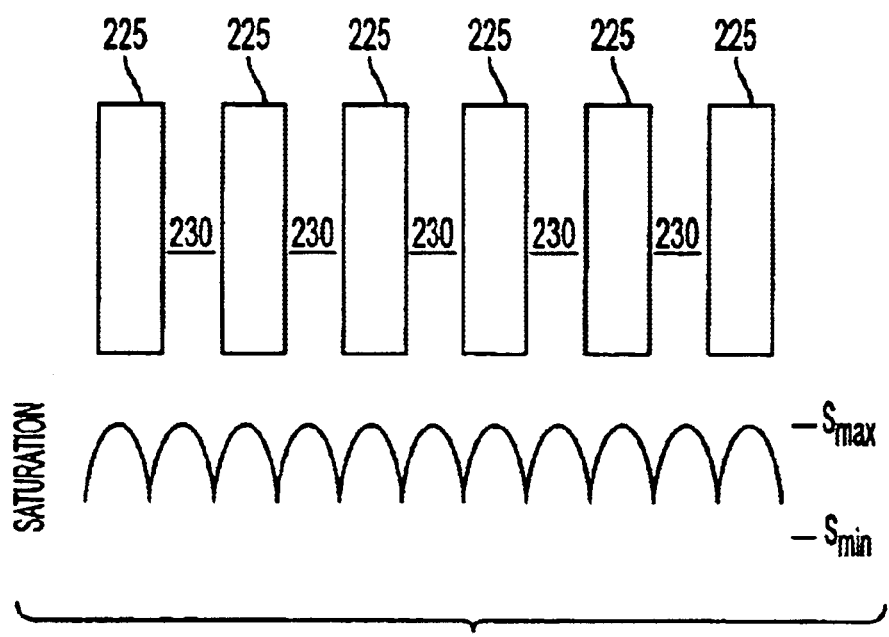
FIG. 8 depict still yet another color grating stimulus along with an alternative saturation profile in accordance with the principles of the present invention.

Alternatively, the saturation can vary from a maximum, $S_{max}$, at the center to a minimum, $S_{min}$ at the edge of each color bar, but in a so-called half wave sinusoidal manner, as depicted in FIG. 8.

For the above color gratings, it is also contemplated that each color bar have the same saturation level, but that the saturation level be varied according to whether the subject correctly identified the orientation of the previous grating stimulus. In this latter manner, as the saturation is varied each color either moves towards or away from gray. In this embodiment, the above control algorithm would be employed, but applied to the saturation level of the colors, rather than the contrast.

Those skilled in the art will readily note that in varying the saturation of the color bars, the red (R), green (G) and blue (B) components of each color will correspondingly vary, which components are used to display the colors to a human observer. In doing so, however, one color bar may appear less or more bright than the other, even though each has the same radiance or luminance. This is so because the luminous efficiency function of the human eye peaks in the green region of the visible spectrum. The eye is less sensitive to red and even less so to blue. Accordingly, it is contemplated that a luminance spectral weighting may be used to compensate for the properties of human vision. Such spectral weighting techniques are well known to those skilled in the art.

It should be clearly understood that the embodiments herein above are merely illustrative of the principles of the invention. Various modifications may be made by those skilled in the art which will embody the principles of the invention and fall within the spirit and the scope thereof.

What is claimed is:

1. A method of measuring the contrast sensitivity of a subject, comprising the steps of:

displaying chains of grating stimuli at randomly interleaved spatial frequencies, each of said grating stimuli consisting of dark and light bars and having one of two alternative orientations;

prompting the subject to identify the orientation of each of said grating stimuli from said one of two alternative orientations; and varying the contrast level of the next grating stimulus according to whether the subject correctly identified the orientation of the previous grating stimulus, wherein a correct response decreases the contrast level of the next grating stimulus in the chain by a first amount, S_down, and whereas an incorrect response increases the contrast level by a second amount, S_up.

2. The method of claim 1 further comprising the step of varying said first and second amounts by which the contrast level is decreased or increased as the measurement progresses, while controlling the ratio between said first and second amounts.

3. The method of claim 2 further comprising the step of finding the best estimation of the contrast threshold at each spatial frequency from the sequence of subject responses to the grating stimuli.

4. The method of claim 3 wherein the step of finding the best estimation includes the step of determining the contrast threshold for which there is a desired percentage of correct responses for the subject in identifying the orientation of the grating stimulus.

5. The method of claim 1 wherein the luminance of said dark and light bars varies in a sinusoidal manner from a maximum $L_{max}$ at the center of the light bar to a minimum, $L_{min}$ at the center of an adjacent dark bar.

6. The method of claim 1 wherein the luminance of said dark and light bars varies in a half-wave sinusoidal manner from a maximum $L_{max}$ at the center to a minimum $L_{min}$ at the edge.

7. The method of claim 1 wherein the luminance of said dark and light bars varies in a square wave manner between a maximum $L_{max}$ to a minimum $L_{min}$.

8. The method of claim 1 wherein the ratio of the first and second amounts S_up/S_down is given by p/(1−p), where p is a target threshold probability, the contrast level converging to a value X_p such that the probability of the subject correctly identifying the orientation of a grating stimulus with the contrast level X_p is p.

9. The method of claim 1 wherein the amounts S_up and S_down are given by S_up=step_size and S_down=step_ size*p/(1−p), where the step_size is a unit of measure by which the contrast level is varied, and p is a target threshold probability for the contrast level to converge to a value X_p such that the probability of the subject correctly identifying the orientation of a grating stimulus with the contrast level X_p is p.

10. The method of claim 1 further comprising the step of displaying a bogus grating stimulus having a sufficiently high contrast level such that the orientation is readily identified by the subject.

11. A method of measuring the contrast sensitivity of a subject, comprising the steps of:
  displaying chains of grating stimuli at randomly interleaved spatial frequencies, each of said grating stimuli consisting of first and second color bars and having one of two alternative orientations;
  prompting the subject to identify the orientation of each of said grating stimuli from said one of two alternative orientations; and
  varying the contrast level of the next grating stimulus according to whether the subject correctly identified the orientation of the previous grating stimulus, wherein a correct response decreases the contrast level of the next grating stimulus in the chain by a first amount, S_down, and whereas an incorrect response increases the contrast level by a second amount, S_up.

12. The method of claim 11 further comprising the step of varying said first and second amounts by which the contrast level is decreased or increased as the measurement progresses, while controlling the ratio between said first and second amounts.

13. The method of claim 11 further comprising the step of finding the best estimation of the contrast threshold at each spatial frequency from the sequence of subject responses to the grating stimuli.

14. The method of claim 13 wherein the step of finding the best estimation includes the step of determining the contrast threshold for which there is a desired percentage of correct responses for the subject in identifying the orientation of the grating stimulus.

15. The method of claim 11 wherein said first and second color bars have complementary colors.

16. The method of claim 11 wherein the luminance of said first and second color bars varies sinusoidally from a maximum $L_{max}$ at the center to a minimum $L_{min}$ at the edge.

17. The method of claim 11 wherein the luminance of said first and second color bars varies in a half-wave sinusoidal manner from a maximum $L_{max}$ at the center to a minimum $L_{min}$ at the edge.

18. The method of claim 11 wherein the luminance of said first and second color bars varies in a square wave manner between a maximum $L_{max}$ to a minimum $L_{min}$.

19. The method of claim 11 wherein the ratio of the first and second amounts S_up/S_down is given by p/(1−p), where p is a target threshold probability, the contrast level converging to a value X_p such that the probability of the subject correctly identifying the orientation of a grating stimulus with the contrast level X_p is p.

20. The method of claim 11 wherein the amounts S_up and S_down are given by S_up=step_size and S_down=step_size*p/(1−p), where the step_size is a unit of measure by which the contrast level is varied, and p is a target threshold probability for the contrast level to converge to a value X_p such that the probability of the subject correctly identifying the orientation of a grating stimulus with the contrast level X_p is p.

21. The method of claim 11 further comprising the step of displaying a bogus grating stimulus having a sufficiently high contrast level such that the orientation is readily identified by the subject.

22. A method of measuring the contrast sensitivity of a subject, comprising the steps of:
  displaying chains of grating stimuli at randomly interleaved spatial frequencies, each of said grating stimuli consisting of first and second color bars and having one of two alternative orientations;
  prompting the subject to identify the orientation of each of said grating stimuli from said one of two alternative orientations; and
  varying the pseudo-color contrast level of the next grating stimulus according to whether the subject correctly identified the orientation of the previous grating stimulus, wherein a correct response decreases the pseudo-contrast level of the next grating stimulus in the chain by a first amount, S_down, and whereas an incorrect response increases the pseudo-contrast level by a second amount, S_up.

23. The method of claim 22 further comprising the step of varying said first and second amounts by which the pseudo-contrast level is decreased or increased as the measurement progresses, while controlling the ratio between said first and second amounts.

24. The method of claim 23 further comprising the step of finding the best estimation of the contrast threshold at each spatial frequency from the sequence of subject responses to the grating stimuli.

25. The method of claim 24 wherein the step of finding the best estimation includes the step of determining the contrast threshold for which there is a desired percentage of correct responses for the subject in identifying the orientation of the grating stimulus.

26. The method of claim 23 wherein the saturation of the first and second color bars varies sinusoidally from a maximum $S_{max}$ at the center to a minimum $S_{min}$ at the edge.

27. The method of claim 23 wherein the saturation of the first and second color bars varies in a half-wave sinusoidal manner from a maximum $S_{max}$ at the center to a minimum $S_{min}$ at the edge.

28. The method of claim 23 wherein the saturation of the first and second color bars varies in a square wave manner between a maximum $S_{max}$ to a minimum $S_{min}$.

29. The method of claim 23 wherein the saturation of said first and second color bars is constant there across.

30. The method of claim 23 wherein said first and second color bars have complementary colors.

31. The method of claim 23 wherein the ratio of the first and second amounts S_up/S-down is given by p/(1−p), where p is a target threshold probability, the pseudo-contrast level converging to a value X_p such that the probability of the subject correctly identifying the orientation of a grating stimulus with the pseudo-contrast level X_p is p.

32. The method of claim 23 wherein the amounts S_up and S_down are given by S_up=step_size and S_down=step_size*p/(1−p), wherein the step_size is a unit of measure by which the pseudo-contrast level is varied, and p is a target threshold probability for the pseudo-contrast level to converge to a value X_p such that the probability of the subject correctly identifying the orientation of a grating stimulus with the pseudo-contrast level X_p is p.

33. The method of claim 23 further comprising the step of displaying a bogus grating stimulus having a sufficiently high pseudo-contrast level such that the orientation is readily identified by the subject.

* * * * *